United States Patent
Spenciner

(10) Patent No.: US 9,486,201 B2
(45) Date of Patent: Nov. 8, 2016

(54) DIRECTIONALLY SPECIFIC BONE ANCHORS AND METHOD

(71) Applicant: DePuy Mitek, LLC, Raynham, MA (US)

(72) Inventor: David B. Spenciner, North Attleboro, MA (US)

(73) Assignee: DEPUY MITEK, LLC, Raynham, MA (US)

(*) Notice: Subject to any disclaimer, the term of this patent is extended or adjusted under 35 U.S.C. 154(b) by 407 days.

(21) Appl. No.: 13/832,875

(22) Filed: Mar. 15, 2013

(65) Prior Publication Data

US 2014/0100609 A1   Apr. 10, 2014

Related U.S. Application Data

(60) Provisional application No. 61/706,199, filed on Sep. 27, 2012.

(51) Int. Cl.
*A61B 17/04* (2006.01)
*A61F 2/08* (2006.01)
*A61B 17/06* (2006.01)

(52) U.S. Cl.
CPC ......... *A61B 17/0401* (2013.01); *A61F 2/0811* (2013.01); *A61B 2017/0409* (2013.01); *A61B 2017/0412* (2013.01); *A61B 2017/0419* (2013.01); *A61B 2017/0427* (2013.01); *A61B 2017/0472* (2013.01); *A61B 2017/06052* (2013.01); *A61B 2017/06057* (2013.01); *A61B 2017/06176* (2013.01); *A61F 2002/0817* (2013.01); *A61F 2002/0847* (2013.01); *A61F 2002/0888* (2013.01)

(58) Field of Classification Search
CPC .................. A61B 17/0401; A61B 2017/0409; A61B 2017/0412; A61B 2017/0419; A61B 2017/0427; A61B 2017/0472; A61B 2017/06057; A61B 17/0642; A61B 17/84; A61B 17/842; A61B 17/846; A61B 17/848; A61B 17/86; A61B 17/8625; A61B 17/863; A61B 17/8635; A61B 17/88; A61B 17/8802; A61B 17/8872; A61B 2017/0411; A61B 2017/044; A61B 2017/06052; A61B 2017/06176; A61F 2/0805; A61F 2/0811; A61F 2002/0817; A61F 2002/0823; A61F 2002/0829; A61F 2002/0835; A61F 2002/0847; A61F 2002/0852; A61F 2002/0585; A61F 2002/0864; A61F 2002/087; A61F 2002/0888; A61F 2002/0841; A61F 2002/0876; A61F 2002/0882
USPC .............. 606/232, 233, 300, 321; 623/13.11, 623/13.12, 13.14
See application file for complete search history.

(56) References Cited

U.S. PATENT DOCUMENTS

| | | |
|---|---|---|
| 3,981,051 A | 9/1976 | Brumlik |
| 4,198,734 A | 4/1980 | Brumlik |
| 4,738,255 A | 4/1988 | Goble |
| 4,899,743 A | 2/1990 | Nicholson |
| 5,053,047 A | 10/1991 | Yoon |
| 5,196,022 A | 3/1993 | Bilweis |
| 5,222,976 A | 6/1993 | Yoon |
| 5,269,783 A | 12/1993 | Sander |

(Continued)

*Primary Examiner* — Darwin Erezo
*Assistant Examiner* — Katherine Schwiker

(57) ABSTRACT

A suture anchor and method is disclosed in which a pair of anchor elements connected by a flexible cord are passed through a piece of soft tissue and embedded deeply into a bone. The cord holds the soft tissue securely to the bone and the anchors are embedded into more dense bone away from the location where the soft tissue contacts the bone.

13 Claims, 8 Drawing Sheets

(56) References Cited

U.S. PATENT DOCUMENTS

| | | |
|---|---|---|
| 5,330,503 A | 7/1994 | Yoon |
| 5,374,268 A | 12/1994 | Sander |
| 5,425,747 A | 6/1995 | Brotz |
| 5,584,859 A | 12/1996 | Brotz |
| 6,146,387 A | 11/2000 | Trott |
| 6,241,747 B1 | 6/2001 | Ruff |
| 6,264,675 B1 | 7/2001 | Brotz |
| 6,290,702 B1 | 9/2001 | Fucci |
| 6,328,758 B1 | 12/2001 | Tornier |
| 6,346,109 B1 | 2/2002 | Fucci |
| 6,599,310 B2 | 7/2003 | Leung |
| 6,692,499 B2 | 2/2004 | Törmälä |
| 6,770,073 B2 | 8/2004 | McDevitt |
| 6,773,450 B2 | 8/2004 | Leung |
| 7,226,468 B2 | 6/2007 | Ruff |
| 7,303,577 B1 | 12/2007 | Dean |
| 7,361,179 B2 | 4/2008 | Rousseau |
| 7,601,164 B2 | 10/2009 | Wu |
| 7,604,657 B2 | 10/2009 | Orbay |
| 7,662,864 B2 | 2/2010 | Kanamathareddy |
| 7,691,135 B2 | 4/2010 | Shaolian |
| 2004/0088003 A1 | 5/2004 | Leung |
| 2005/0182405 A1 | 8/2005 | Orbay |
| 2005/0182406 A1 | 8/2005 | Orbay |
| 2006/0235413 A1 | 10/2006 | Denham |
| 2006/0253119 A1* | 11/2006 | Berberich et al. ............ 606/72 |
| 2007/0005109 A1* | 1/2007 | Popadiuk et al. ............ 606/228 |
| 2007/0038222 A1 | 2/2007 | Bhatnagar |
| 2007/0038249 A1* | 2/2007 | Kolster ....................... 606/228 |
| 2007/0093835 A1 | 4/2007 | Orbay |
| 2007/0293866 A1 | 12/2007 | Stoeckel |
| 2008/0009871 A1 | 1/2008 | Orbay |
| 2008/0161805 A1 | 7/2008 | Saravia |
| 2009/0118734 A1* | 5/2009 | Bhatnagar ............ A61B 17/064 606/75 |
| 2009/0125070 A1 | 5/2009 | Sixto, Jr. |
| 2009/0192545 A1* | 7/2009 | Workman ................... 606/232 |
| 2009/0287245 A1 | 11/2009 | Ostrovsky |
| 2010/0030135 A1 | 2/2010 | Mitchell |
| 2011/0213417 A1* | 9/2011 | Foerster et al. ............ 606/232 |
| 2013/0006276 A1* | 1/2013 | Lantz ................. A61B 17/0401 606/144 |

* cited by examiner

DIRECTIONALLY SPECIFIC BONE ANCHORS AND METHOD

BACKGROUND

This application relates to bone anchors and more specifically to bone anchors adapted for fixation within soft bone.

A common surgical procedure is the attachment of soft tissue to bone. This is typically achieved by embedding a bone screw or anchor into the bone adjacent the soft tissue and then approximating the soft tissue to the bone via a length of suture attached to the anchor and passed through the bone. In some procedures the anchor itself is attached to the soft tissue and embedded into the bone to affix the soft tissue to the bone.

Such procedures rely upon achieving strong fixation between the anchor and the bone. However, in many instances the quality of the bone is insufficient for adequate fixation of the anchor. For, instance bone mineral density decreases with age and many older patients lack sufficient bone quality for a typical procedure. Additional anchors can be employed, such as the use of a second row of anchors in a rotator cuff repair, but the quality of the bone under the second, lateral, row is often lower still. Larger diameter anchors are also employed to improve fixation but that adds additional trauma to the procedure. These problems are of particular concern in rotator cuff repairs where bone quality at the site of the cuff reattachment is all too often poor but the stresses on the rotator cuff require a strong fixation to ensure proper healing.

SUMMARY OF THE INVENTION

The present invention overcomes these and other limitations of the prior art in a simple and elegant design.

A method according to the present invention provides for attaching a piece of soft tissue to a bone. The method comprises the steps of: embedding a first anchor into the bone adjacent the soft tissue, the first anchor comprising a first distal end and a trailing elongated first flexible body, the first distal end being passed into the bone along a first pathway having a first entrance into the bone adjacent the soft tissue, a first section of the first pathway adjacent the first entrance comprising cancellous bone of a first density and a second section of the first pathway being deeper into the bone from its first section and having cancellous bone of a second density higher than the first density, the first distal end being positioned in the second section; and holding the soft tissue to the bone adjacent the first entrance via affixation of the soft tissue to the first flexible body.

The method preferably further comprises embedding a second anchor into the bone adjacent the soft tissue, the second anchor comprising a second distal end and a trailing elongated second flexible body, the second distal end being passed into the bone along a second pathway having a second entrance into the bone adjacent the soft tissue, a first section of the second pathway adjacent the second entrance comprising cancellous bone of a third density and a second section of the second pathway being deeper into the bone from its first section and having cancellous bone of a fourth density higher than the third density, the second distal end being positioned in the second section of the second pathway; and holding the soft tissue to the bone adjacent the second entrance via affixation of the soft tissue to the second flexible body.

Preferably, the first flexible body and second flexible body are interconnected prior to being embedded into the bone.

In one aspect of the invention, fixation of the first flexible body into the bone is enhanced with a plurality of barbs extending from the first flexible body and engaging the bone.

Preferably, the first flexible body is pushed into the bone via a rigid introducer connected to the first distal end, the introducer then being removed after the step of embedding the first anchor into the bone. The first distal end preferably comprises a rigid tip having a proximally facing surface. The introducer is then pushed against the proximally facing surface to push the first flexible body into the bone. Preferably, that portion of the introducer inserted into the bone has a maximum size of about 15 gauge. In an aspect of the invention, a plurality of barbs extend from the first flexible body and are held in a retracted position against the first flexible body by the introducer.

Preferably, the first anchor is driven into the bone without first preparing a pilot hole for it.

Preferably, the first path curves. In one aspect of the invention, the soft tissue is a rotator cuff tendon and the bone is a humeral head. In such event, the first path preferably curves medially. Preferably, the first path extends at least half the width of the humeral head.

DETAILED DESCRIPTION

Figure 1:
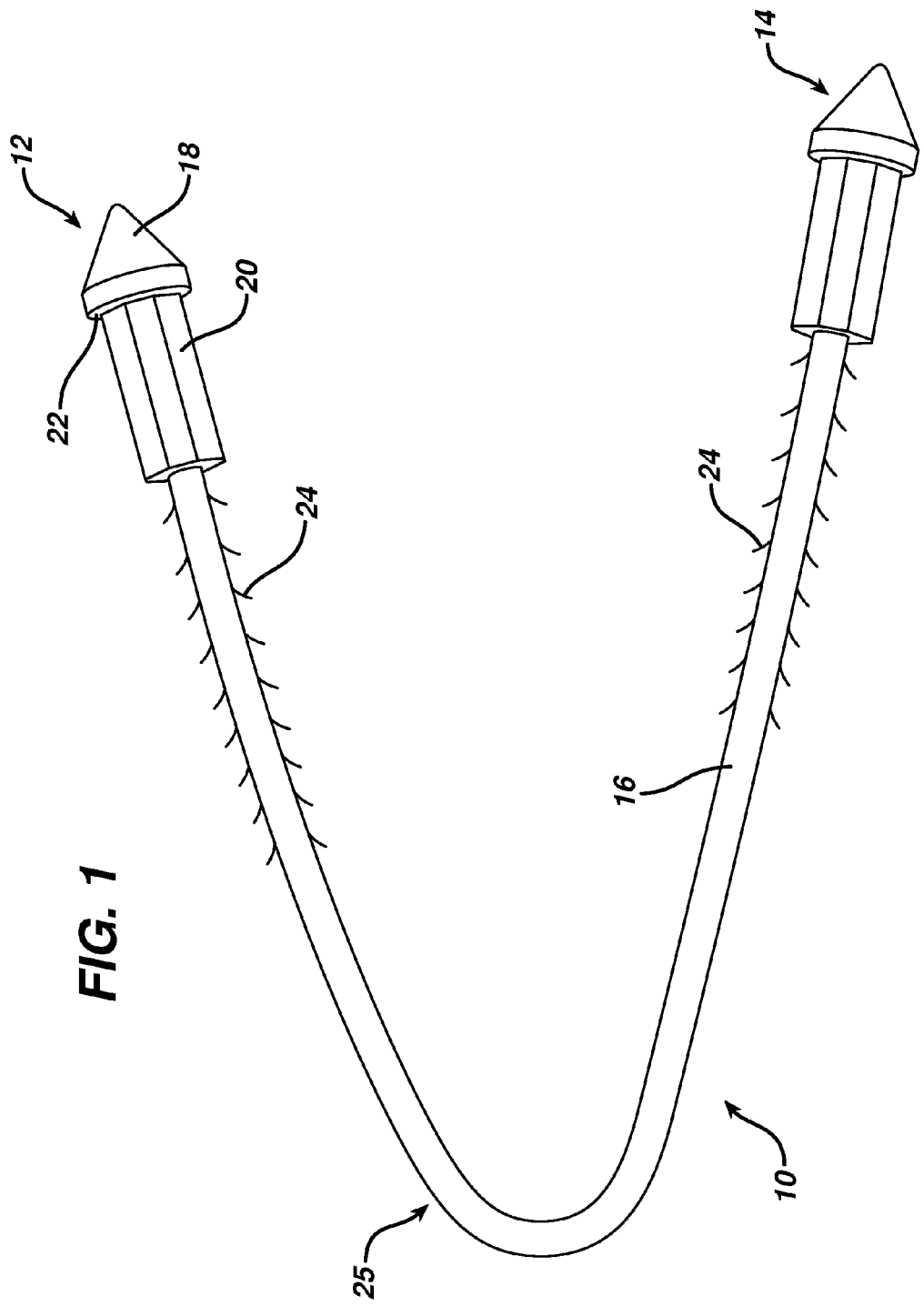
FIG. 1 is a top plan view of a suture anchor according to the present invention.

FIG. 1 shows a suture anchor 10 according to the present invention. It comprises a first anchor element 12 and second anchor element 14 interconnected by a flexible cord 16. Each anchor member 12, 14 comprises a distal conical tip 18 and a proximal tubular body 20 swaged onto the cord 16. A proximally facing annular flange 22 interfaces between the tip 18 and the body 20. A plurality of flexible barbs 24 can optionally be disposed on the cord 16 adjacent the anchor elements 12 and 14 with a central section 25 being free of barbs.

Figure 2:
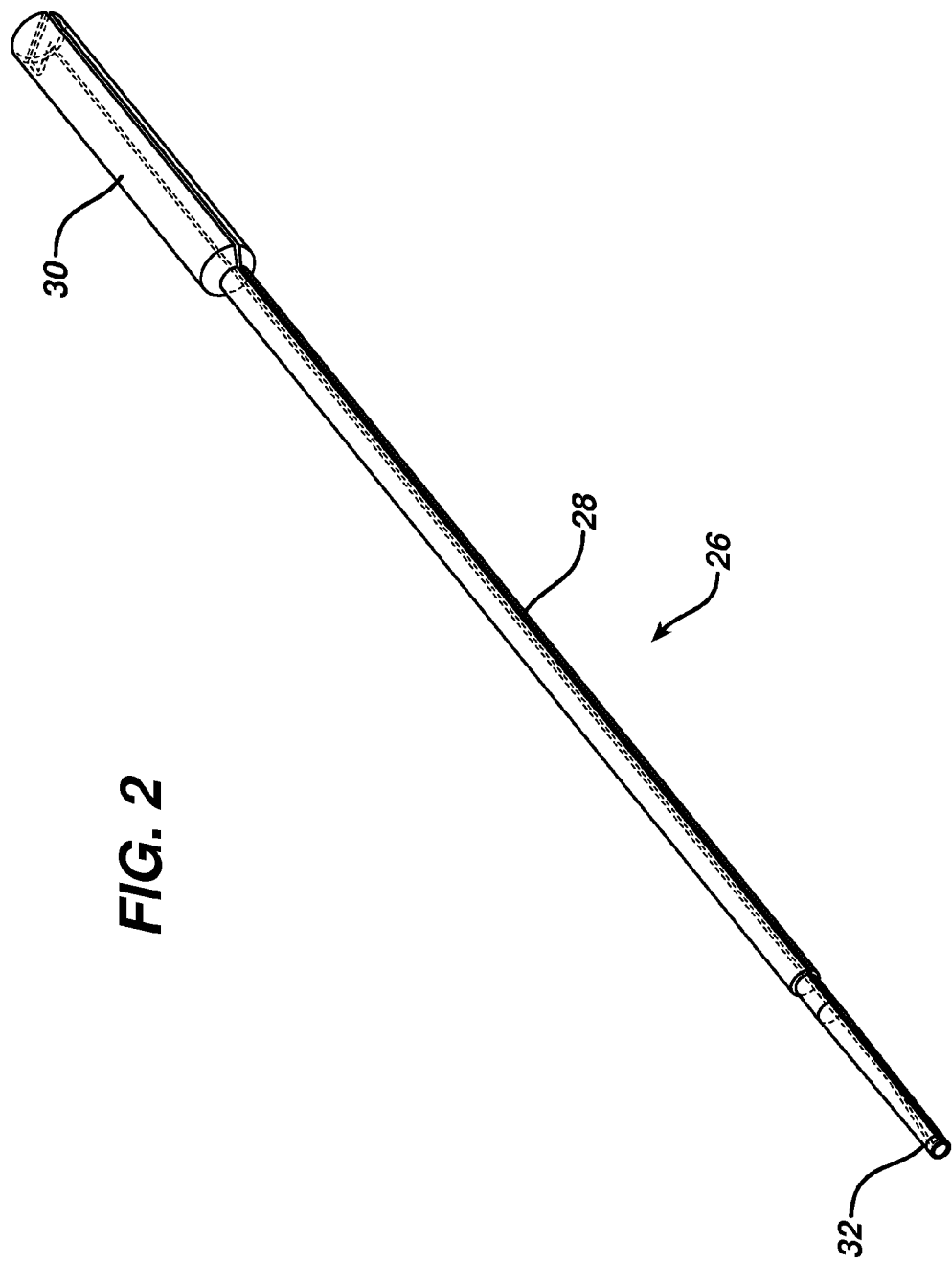
FIG. 2 is a perspective view of an inserter for use with the suture anchor of FIG. 1.
Figure 3:
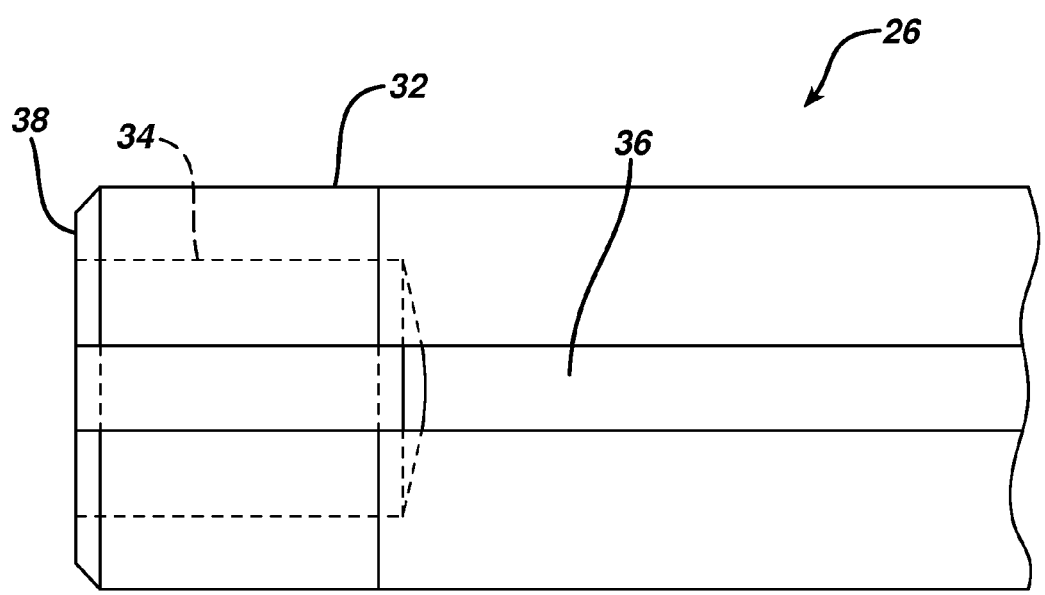
FIG. 3 is a side elevation view of the tip of the inserter of FIG. 2.
Figure 4:
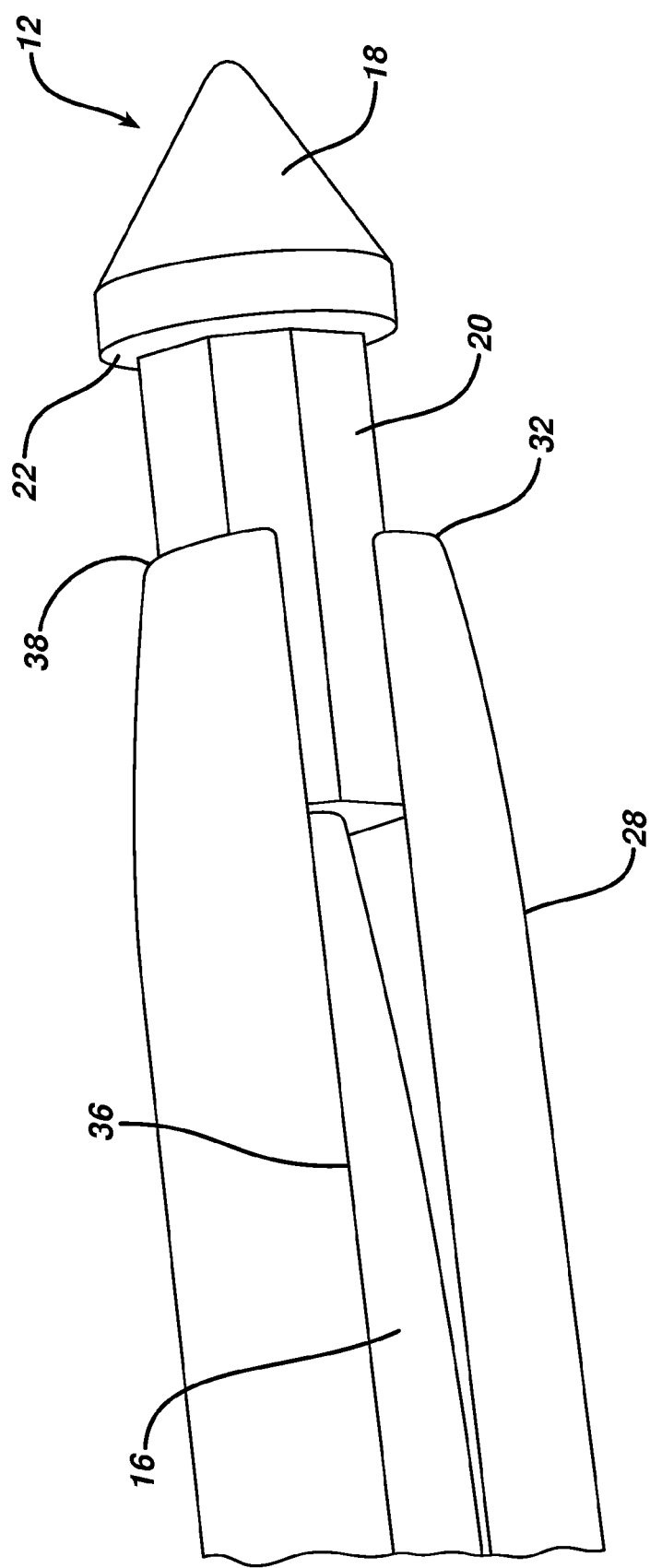
FIG. 4 is a side elevation view of tip of the inserter of FIG. 2 with the suture anchor of FIG. 1 loaded therein.

Turning also now to FIGS. 2 and 3, an inserter 26 comprises an elongated shaft 28 having a proximal handle 30 and narrowing to a distal tip 32. A distally facing socket 34 is sized to receive the body 20 of one of the anchor elements 12, 14. An axial slotted cannulation 36 runs from the tip 32 up the shaft 28 to accommodate and allow the lateral release of the cord 16. A distal end 38 of the inserter, surrounding the socket 34, is adapted to abut the flange 22 on the anchor elements 12, 14, as best seen in FIG. 4. The anchor element 12 is shown partially pulled out of the socket in FIG. 4 to more clearly show the flange 22 and distal end 38. In use they will abut one another. The barbs 24 are held in a retracted position within the cannulation 36.

Figure 5:
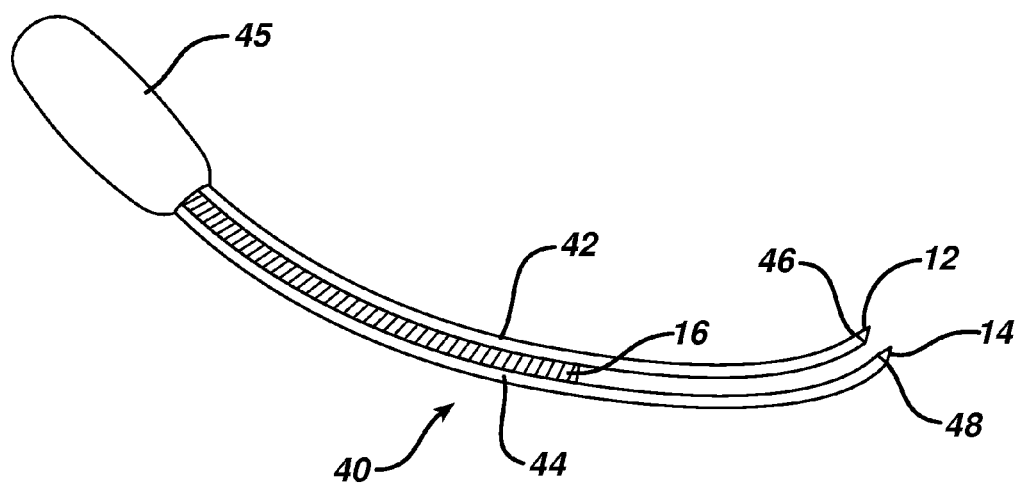
FIG. 5 is a perspective view of an alternative inserter according to the present invention for use with the suture anchor of FIG. 1.

FIG. 5 shows an alternative embodiment of an inserter 40 having first and second parallel curved shafts 42 and 44, and a handle 45, with the first anchor element 12 loaded into a tip 46 of the first shaft 42 and the second anchor element 14 loaded into a tip 48 of the second shaft 44.

Figure 6:
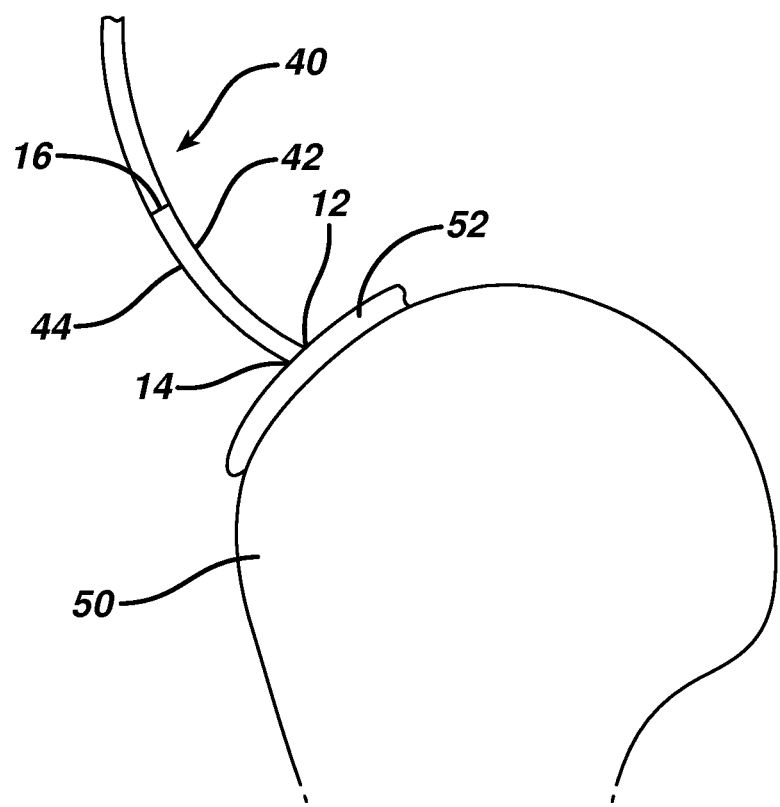
FIG. 6 is a side elevation view of a humeral head showing the inserter of FIG. 5 in position for use.
Figure 7:
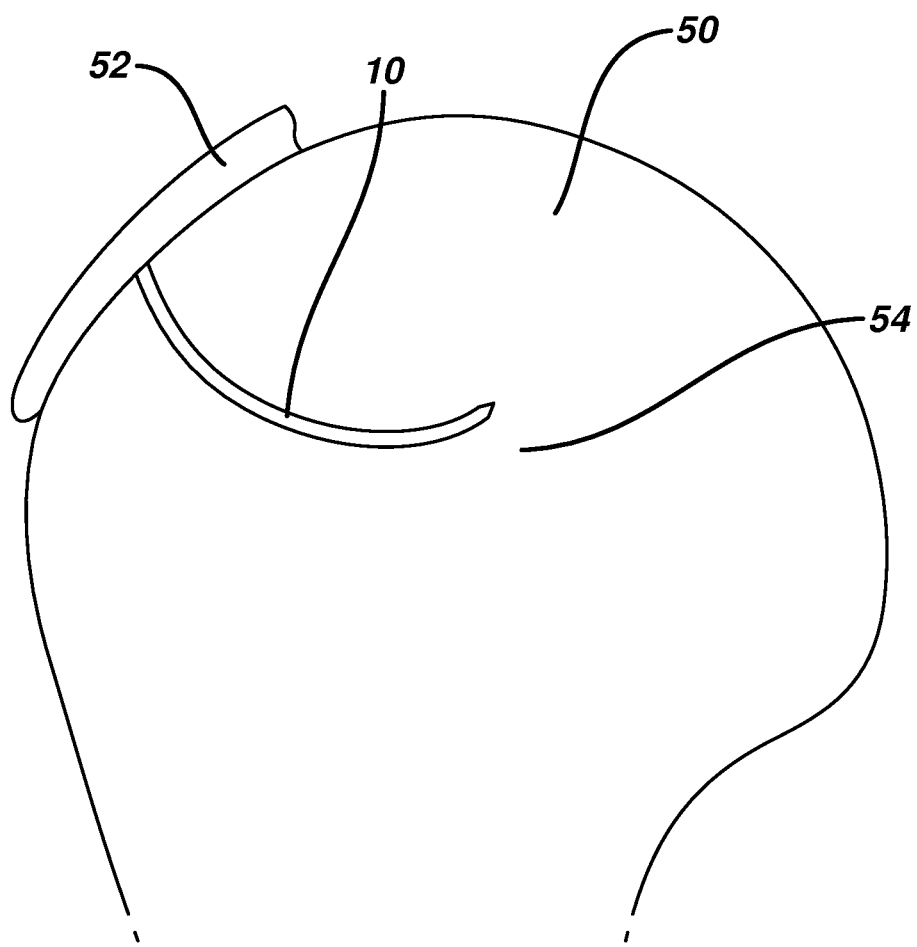
FIG. 7 is a side elevation view of the humeral head of FIG. 6 in cross-section.

FIGS. 6 and 7 illustrate a humeral head 50 and rotator cuff tendon 52. To effect a repair, the tendon 52 is approximated to the desired location with a tendon grasper (not shown). With the tendon 52 in place, the, the pre-loaded inserter 40 is placed against the tendon and its angle adjusted to achieve a proper trajectory into the humeral head 50. The inserter 40 is then hammered to drive the shafts 42 and 44 into the humeral head 50 thereby driving the anchor elements 12 and 14 therein until the central section 25 of the cord 16 snugly holds the tendon 52 to the humeral head 50. The anchor elements 12 and 14 travel in from the tuberosity adjacent the tendon 52 and travel medially along a curved path but stop prior to breeching the articular surface and lodge deeply into the dense interior bone. The desired depth and angle can be determined via pre-operative X-rays or other assessment of the geometry of the humeral head 50. Depth markings, stops or other techniques can be employed to ensure proper depth. Preferably, the inserter 40 can be provided to a surgeon in various lengths and perhaps levels of curvature (including straight) so that the surgeon can choose based upon the geometry of the patient's humeral head 50. After the anchor elements 12 and 14 are inserted to the desired location, the inserter 40 is removed leaving the suture anchor 10 in place.

FIG. 7 shows a typical bone density distribution in an osteoporotic bone, illustrating the advantages of the present invention. The bone density in the head 50 near tendon 52 is significantly less than in a more medial bone area 54. A typical prior suture anchor would be placed into the less dense bone just below the tendon 52 or just lateral of its edge, also of low bone density. In contrast, the suture anchor 10 travels deeply and medially into the humeral head into the more dense bone area 54.

Figure 8:
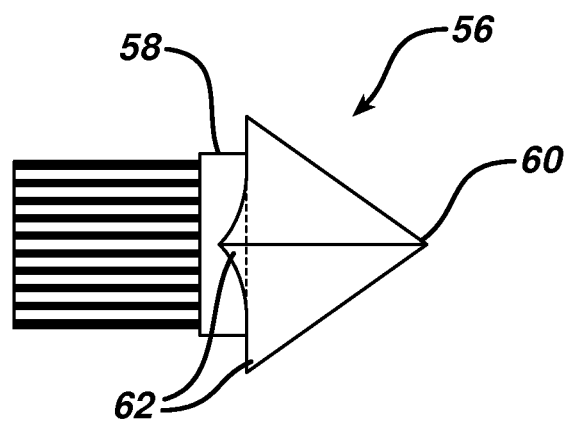
FIG. 8 is a side elevation view of an alternative embodiment of an anchor element of a suture anchor according to the present invention.

The anchor elements 12 and 14 can be smaller than a traditional suture anchor which would be employed to hold the same tendon 52 due to the enhanced holding from their depth in the tissue and the superior bone into which they are placed. For a rotator cuff repair they may be sized to fit with an introducer the equivalent of a 15 to 18 gauge needle. The anchor elements 12 and 14 can be formed of materials suitable for suture anchors such as stainless steel, titanium, PEEK, Polylactic Acid (PLA), Polylactic/polyglycolic Acid (PLGA), and mixtures with TriCalcium Phosphate (TCP) along with other materials as will be appreciated by those of skill in the art. FIG. 8 shows an alternative embodiment of an anchor element 56 having a body 58 and sharp tip 60 with multiple barbs 62 to enhance the holding of the anchor element 56 into bone. Alternatively, an anchor element could be detachable from the cord 16, such as being part of an inserter, or be quickly absorbable into the tissue, in either event to not add appreciable to the fixation but rather leave that function to the cord 16.

The cord 16 can be standard suture, or barbed suture, of either the absorbent or non-absorbent varieties. ORTHOCORD suture available from DePuy Mitek of Raynham, Mass. could be employed. The cord 16 could also be a metal wire, particularly a braided wire preferably with barbs. Alternatively, or additionally, the suture or wire could be treated or coated to enhance its coefficient of friction with bone.

To prevent cheese-wiring of the cord 16 into the bone it could be made broader where it exits the humeral head 50, such as by being of larger diameter or wider and flatter such as a ribbon. Grommets (not shown) could be received on the inserter shaft 28 and embedded into the humeral head 50 thereby where the cord 16 exits the humeral head so that the cord 16 would rub against the grommets rather than the bone at this point. Rather than the cord 16 affixing itself to the tendon 52 or other tissue to be attached, it could have a trailing suture, either attached as provided or through an eyelet or other suture attachment on the cord 16, which is used to connect to the tissue.

The invention preferably includes two or more anchor elements 12 and 14 interconnected by a cord 16. However, it is envisioned that it could comprise a single anchor element with a cord trailing therefrom. The cord could be connected, such as after the anchor element is implanted, with another cord from another single anchor element, suture anchor or to a different type of suture anchor or to a suture from a different suture anchor. The cord, could be suture and it could be passed up from the implanted anchor element, out through the tendon 52 and over to a self-locking suture anchor (such as disclosed in U.S. Pat. No. 6,770,073) implanted at a different location, perhaps lateral of the tendon 52, and then tensioned and locked to the self-locking anchor. One such self-locking anchor is the VERSALOK suture anchor available from DePuy Mitek of Raynham, Mass. While described most fully for a rotator cuff repair it is envisioned that the present invention would be useful for many other soft tissue repair procedures, especially where bone quality at the site of repair is degraded. It may also have utility for fracture or other bone repairs.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof. For instance, rather than having a fixed length cord 16 spanning two suture anchors 12 and 14, the cord 16 could be of adjustable length or be separated into portions which could then be tied or otherwise connected together or to other suture anchors etc. Rather than employ barbs 24 and or even the anchor elements 12 and 14 fixation could come from a portion of suture or attachment that expands in contact with bodily fluid. The anchor elements 12 and 14 can comprise any type of body that an inserter can push against for delivery into the bone, e.g., an overhand knot, a folded suture, thermally reformed suture tips, etc.

What is claimed is:

1. A method for attaching a piece of soft tissue to a bone, the method comprising the steps of:
    embedding a first anchor into the bone adjacent the soft tissue, the first anchor comprising a first distal end and a trailing elongated first flexible body, the first distal end being passed into the bone along a first pathway having a first entrance into the bone adjacent the soft tissue, a first section of the first pathway adjacent the first entrance comprising cancellous bone of a first density and a second section of the first pathway being deeper into the bone from its first section and having cancellous bone of a second density higher than the first density, the first distal end being positioned in the second section; and holding the soft tissue to the bone adjacent the first entrance via affixation of the soft tissue to the first flexible body.

2. A method according to claim 1 and further comprising embedding a second anchor into the bone adjacent the soft tissue, the second anchor comprising a second distal end and a trailing elongated second flexible body, the second distal end being passed into the bone along a second pathway having a second entrance into the bone adjacent the soft tissue, a first section of the second pathway adjacent the second entrance comprising cancellous bone of a third density and a second section of the second pathway being deeper into the bone from its first section and having cancellous bone of a fourth density higher than the third density, the second distal end being positioned in the second section of the second pathway; and holding the soft tissue to the bone adjacent the second entrance via affixation of the soft tissue to the second flexible body.

3. A method according to claim 2 wherein the first flexible body and second flexible body are interconnected prior to being embedded into the bone.

4. A method according to claim 1 wherein fixation of the first flexible body into the bone is enhanced with a plurality of barbs extending from the first flexible body and engaging the bone.

5. A method according to claim 1 wherein the first flexible body is pushed into the bone via a rigid introducer connected to the first distal end, the introducer being removed after the step of embedding the first anchor into the bone.

6. A method according to claim 5 wherein the first distal end comprises a rigid tip having a proximally facing surface and wherein the introducer is pushed against the proximally facing surface to push the first flexible body into the bone.

7. A method according to claim 5 wherein a portion of the introducer is inserted into the bone during the step of pushing the first flexible body into the bone and the portion of the introducer inserted into the bone has a maximum size of about 15 gauge.

8. A method according to claim 5 wherein a plurality of barbs extend from the first flexible body and are held in a retracted position against the first flexible body by the introducer and are then extended from the flexible body upon release from the introducer.

9. A method according to claim 1 wherein the first anchor is driven into the bone without first preparing a pilot hole for it.

10. A method according to claim 1 wherein the first path curves.

11. A method according to claim 1 wherein the soft tissue is a rotator cuff tendon and the bone is a humeral head.

12. A method according to claim 11 wherein the first path curves medially.

13. A method according to claim 11 wherein the first path extends at least half way through the humeral head.

* * * * *